United States Patent [19]

Farrer Velazquez

[11] Patent Number: 5,474,518
[45] Date of Patent: Dec. 12, 1995

[54] CORRECTIVE DEVICE OF URINARY INCONTINENCE IN WOMEN

[76] Inventor: Francisco Farrer Velazquez, Gracian, 18, Saragossa, Spain, 50300

[21] Appl. No.: 381,018

[22] Filed: Jan. 31, 1995

Related U.S. Application Data

[63] Continuation of Ser. No. 131,487, Oct. 4, 1993.

[30] Foreign Application Priority Data

Oct. 5, 1992 [ES] Spain .................... 9201960

[51] Int. Cl.⁶ ........................................ A61F 2/02
[52] U.S. Cl. ...................... 600/30; 128/DIG. 25
[58] Field of Search ............. 600/29–32; 128/DIG. 23, 128/897–899

[56] References Cited

U.S. PATENT DOCUMENTS 5,041,077  8/1991  Kulick ..................... 128/DIG. 25

FOREIGN PATENT DOCUMENTS

| 18442/83 | 3/1984 | Australia . |
| 264258 | 4/1988 | European Pat. Off. . |
| 2021359 | 11/1991 | European Pat. Off. . |
| 2035308 | 4/1993 | European Pat. Off. . |
| 3720858 | 1/1989 | Germany .................... 128/DIG. 25 |
| WO91/0069 | 6/1991 | WIPO . |

*Primary Examiner*—Lee S. Cohen
*Assistant Examiner*—John P. Lacyk
*Attorney, Agent, or Firm*—Darby & Darby

[57] ABSTRACT

A device for correcting urinary incontinence in women, in such a way that the implantation of said device is carried out by a surgical technique of vesical suspension, is basically comprised of a box that is implanted in the patient's body and an external handle that permits the elements of the box to be operated from outside the body, so that the box houses a drum with a toothed wheel that gears in a worm, while the external handle is formed by a body, in whose inside hole is housed a second body that operates by its end upon the head of the worm.

3 Claims, 4 Drawing Sheets

CORRECTIVE DEVICE OF URINARY INCONTINENCE IN WOMEN

This is a continuation of application Ser. No. 8/131,487, filed Oct. 4, 1993, now abandoned.

OBJECT OF THE INVENTION

As is expressed in the title of the present specification, the following invention consists of a corrective device of urinary incontinence in women, carried out by means of surgery and which is fundamentally based on a box of biocompatible material and an external handle of the same, in such a way that said box remains placed inside the patient's body, housed inside it a drum with a toothed wheel that gears in a worm operable from outside of the body by means of an external handle.

The cited external handle makes it possible to adjust with total precision the thread or twisted cord upon the vesical neck, first during surgery itself and subsequently in the postoperative period to avoid urinary incontinence.

The box or mechanical element placed inside the body houses inside it a worm geared in a toothed wheel of the drum upon which the twisted cord or thread that exerts pressure on the vesical neck is wound, in such a way that upon operating the external handle upon the worm, permits perfect adjustment of the length of the thread.

For this purpose, the housing in which the worm and the toothed wheel with the drum for winding the thread or twisted cord are located, has two ducts toward the outside through which the thread or twisted cord that is knotted or that remains fastened to the drum passes.

BACKGROUND OF THE INVENTION

Surgery to treat urinary incontinence in women, by means of the vesical suspension technique is carried out in the following manner:

Preparation: shaving, disinfecting the skin and vaginal mucous membrane.

Position: gynecologic.

Incision: transversal, suprapubic some 4 cms. long, covering all the subcutaneous cellular tissue coming close to the anterior aponeurosis of the anterior straight abdominal muscles.

Technique: Insertion by means of cystoscopic control of the two leading needles following a paraurethral path, adapted to the concavity of the posterior surface of the pubis, from the aponeurosis of the straight muscles up to the anterior surface of the vagina, where they are externalized with a separation of some 2 cm.

Transversal dissection of the vaginal mucous membrane between the two outlet points of the leading needles for the purpose of preparing a submucous tunnel.

Threading the corresponding needles of both ends of synthetic or silk thread suture to which a silicone tube about 4 cm. long will have been previously inserted for the purpose of cushioning the urethra.

Exteriorization of both ends of the suture above the aponeurosis of the straight muscles, by means of pulling on the leading needles.

Suture with loose stitches the vaginal incision.

Pulling and knotting the synthetic or silk thread suture.

Under cystoscopic control the suitable closing of the vesical neck and recovery of the posterior urethrovesical angle will be checked.

Suture of the subcutaneous plane with loose stitches. Intradermal suture skin, with loose silk stitches.

Permanent vesical catheter.

DESCRIPTION OF THE INVENTION

The present specification describes a corrective device of urinary incontinence in women, fundamentally based on a box and external handle like a screwdriver, so that the box of biocompatible material and with a fusiform section without sharp edges, remains placed inside the patient's body and inside of which a worm that gears in a toothed wheel linked to the drum for winding the thread or twisted cord that will exert pressure on the vesical neck is housed, so that upon said worm one can operate from outside the body in order to adjust the tightness of the thread or twisted cord.

The surgery to implant the corrective device is done in the same way as the operation described using the vesical suspension technique.

The cited box has a pair of ducts that communicate with the housing of the worm and of the drum with the toothed wheel to permit the passing of the thread or twisted cord and knotting thereof or fastening thereof to the drum so that it winds around itself when the worm is actuated by means of the external handle.

In this way, upon actuating the worm by means of the external handle, the two ends of the thread or twisted cord move together, thus preventing rubbing with tissues.

The external handle is formed by a hollow body inside of which there is an element that actuates upon the head of the worm for the anchoring thereof, actuating by means of the screwdriver to attain said anchoring. Thus, the hollow rigid or flexible material body remains connected by one side to the head of the worm and by the other side it remains outside of the body so that the same can be actuated.

The inside body of the handle has a position that permits the release of the same and another one that fastens the handle to the worm, thus allowing it to be actuated and adjusting the pressure of the thread or twisted cord upon the vesical neck.

Likewise, the external handle can be replaced by a guide thread that connects the head of the actuating worm with the outside, and by means of which the external handle can be inserted in a perfectly guided manner through the laparotomy incision, if necessary.

When it is determined that the corrective device has been perfectly adjusted and the incontinence no longer takes place, the external element is removed as no subsequent adjustment is necessary.

In order to complement the description that is going to be made hereinafter and for the purpose of providing a better understanding of the characteristics thereof, a set of drawings in whose figures the most significant details of the invention are represented in an illustrative and non-restrictive manner is attached to the present specification.

DESCRIPTION OF A PREFERRED EMBODIMENT

Figure 1:
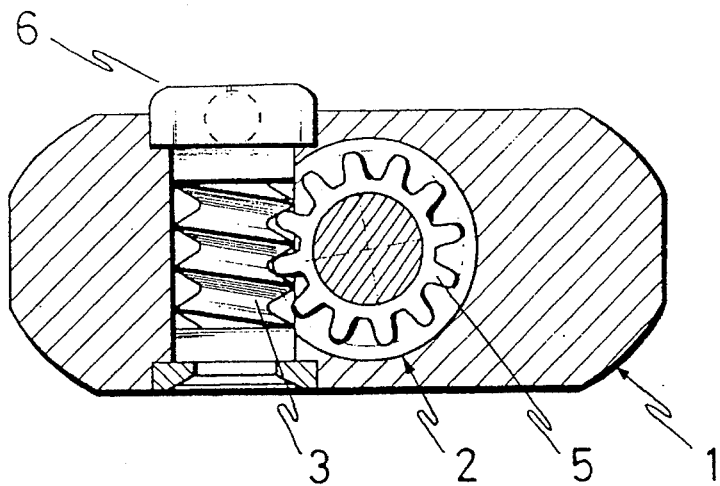
FIG. 1. It shows a view according to a section of the box that houses the drum with the toothed wheel that gears in the worm which is actuated to adjust the tightness of the twisted cord or thread that presses on the vesical neck.
Figure 2:
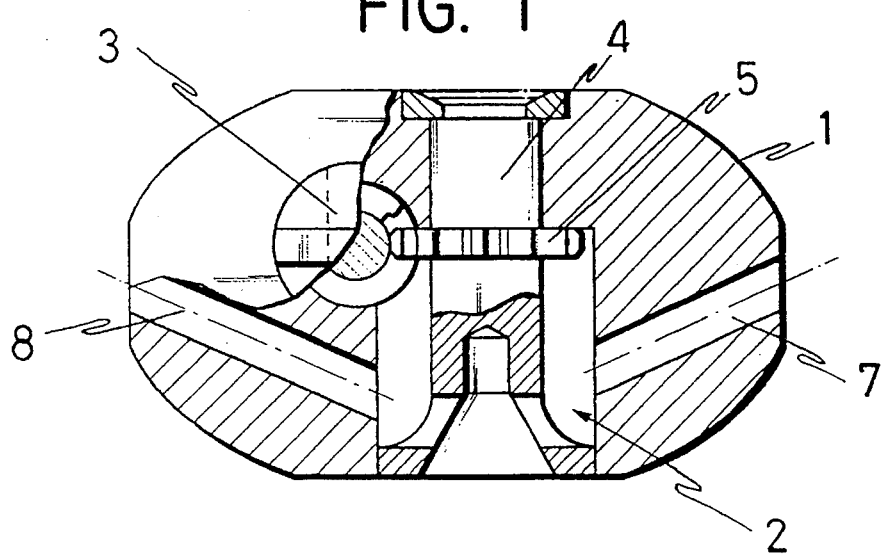
FIG. 2. It shows a section of the box that houses the drum with the toothed wheel, that gears in the worm, according to a plane turned 90° with regard to the previous figure and in which we can see the ducts where the ends of the thread or twisted cord pass in order to be knotted and/or fastened to the drum.
Figure 3:
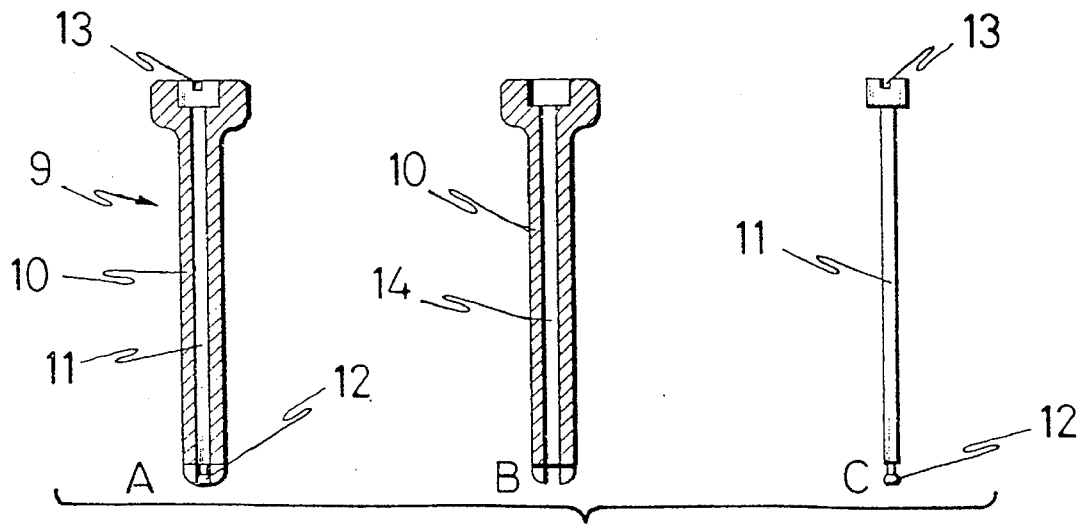
FIG. 3. It shows views of a varied embodiment according to a vertical plane of the external handle with the inside piece that actuates upon the worm upon being handled by the screwdriver.
Figures 4, 5:
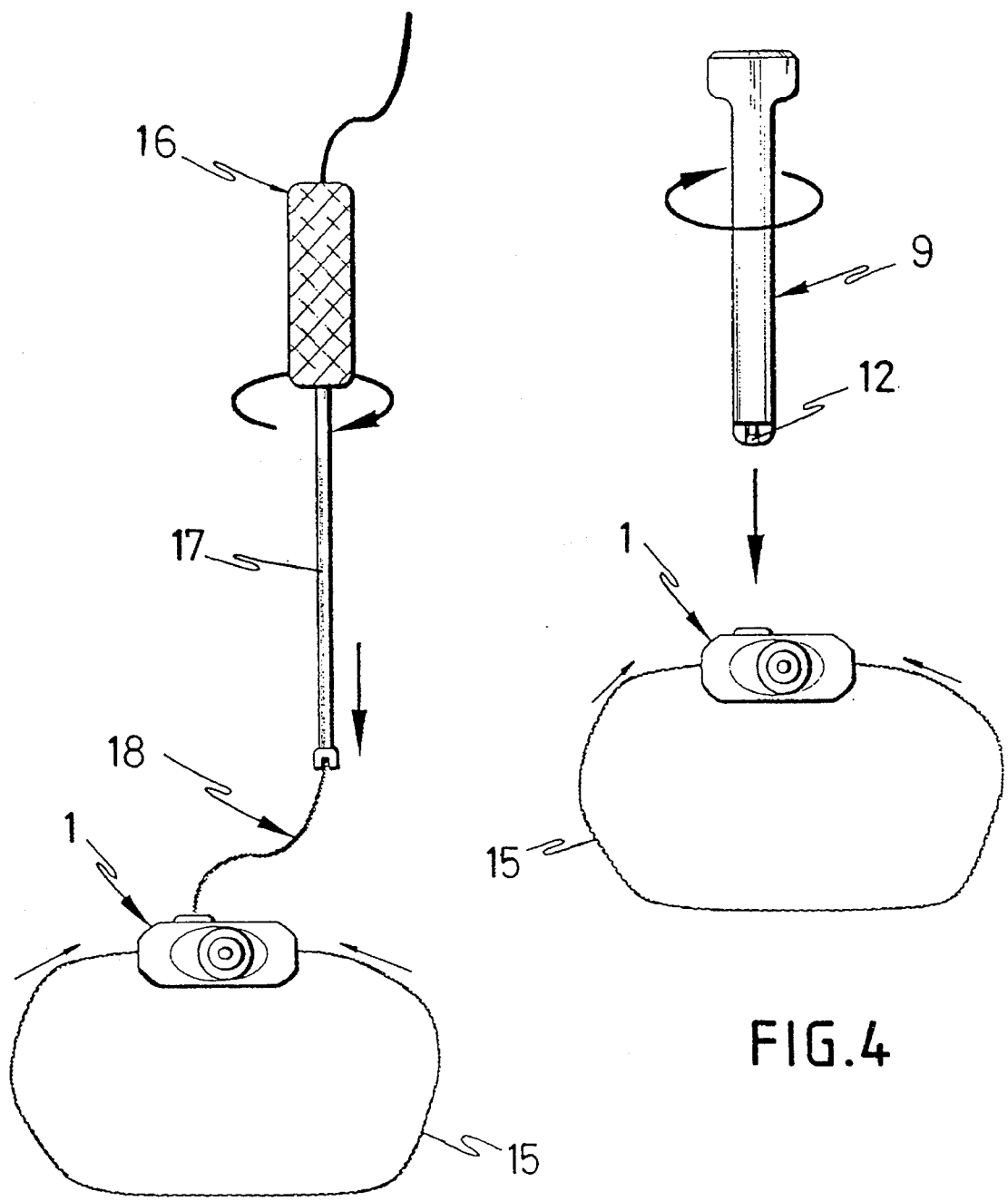
FIG. 4. It shows a view of the box with the thread or twisted cord that presses on the vesical neck and the way that the external handle will couple to the head of the worm.
FIG. 5. It shows a varied embodiment in which the external handle is inserted by means of a guide thread.
Figure 6:
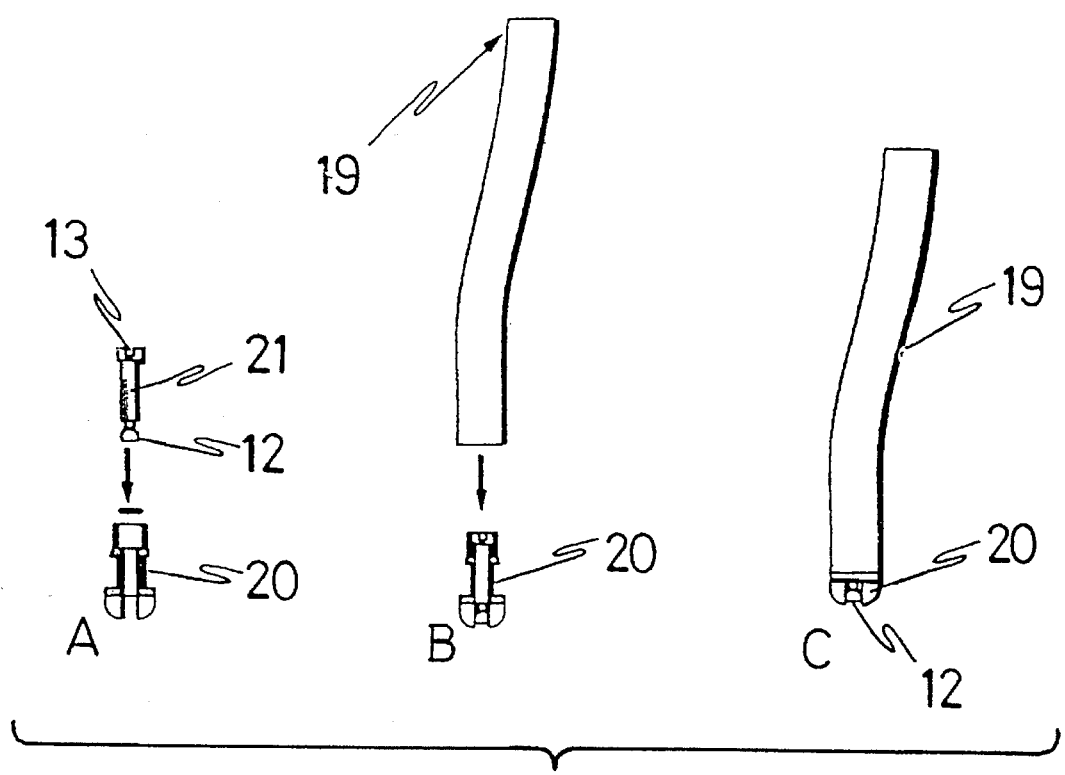
FIG. 6. It shows views of a varied embodiment of the external handle, in which two bodies to permit operation thereof on the head of the worm are joined in the inside end of the outside body made of flexible material, such as silicone, upon inserting a screwdriver or similar instrument inside the flexible tube until the inside head that gears in the worm is actuated.
Figure 7:
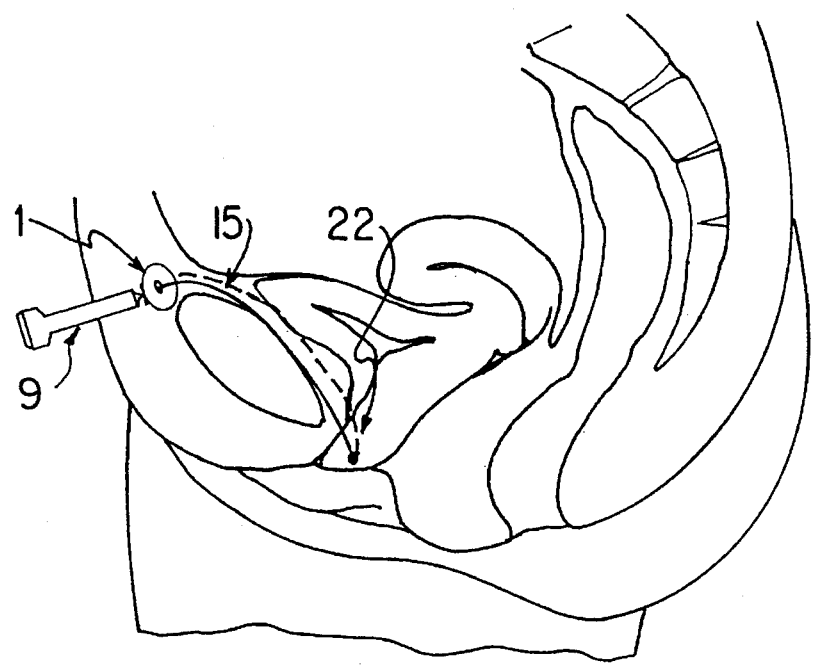
FIG. 7. It shows a sectioned view of the way in which the box remains implanted with the thread or twisted cord upon the vesical neck, and the external handle which permits the worm to be actuated in order to adjust the pressure of the thread or twisted cord from outside the body.
Figure 8:
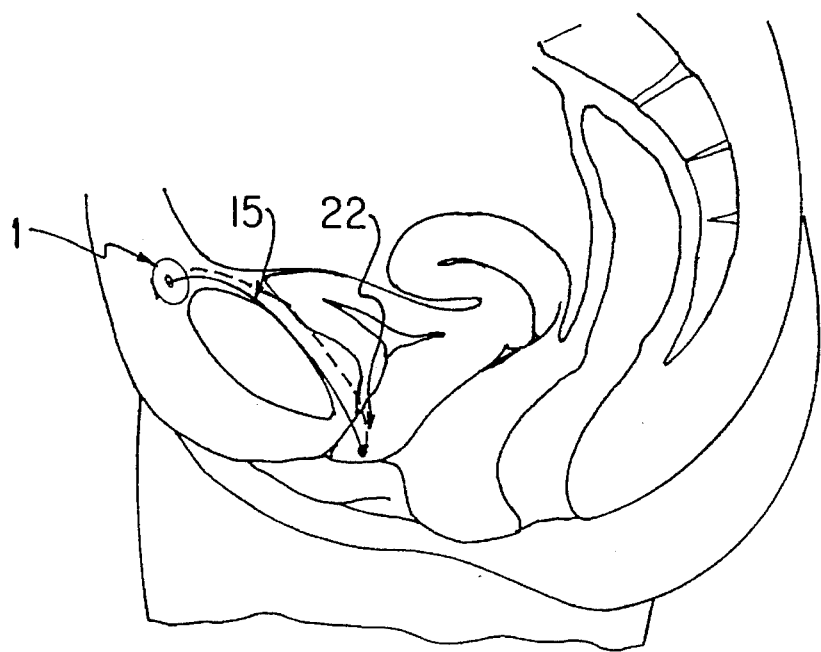
FIG. 8. It shows a sectioned view similar to that of the previous figure, in which the external handle has already been removed since it has been achieved that the pressure of the thread or twisted cord upon the vesical neck suffices to avoid urinary incontinence.

In view of the commented figures and in accordance with the numbering used, we can see how the corrective device of urinary incontinence in women is based on box (1) in whose inside housing (2) a drum (4) with a toothed wheel (5) that gears in a worm (3) and an external handle (9) that permits actuating the head (6) of the worm (3) is housed.

The box (1) implanted in the patient's body is made of biocompatible material and has a fusiform section without sharp edges and is provided with a pair of ducts (7) and (8) opposite each other to pass the ends of the thread (15) to knot it or fasten it to the drum (4) to permit the winding thereof around it, upon actuating the worm (3) by means of the external handle (9.)

The external handle (9) is formed by a hollow body (10) in whose axial central hole (14) the body (11) whose inside end (12) is coupled to the worm (3) is housed and whose other end (13) has a groove so that the screwdriver or similar actuating device is coupled.

The body (11) permits two positions to be adopted avoiding accidental release of the external handle (9) with regard to the head (6) of the worm, as well as its action upon the same, to cause rotation thereof in one direction or the other.

Hence, during surgery the box (1) remains implanted inside the patient's body and the thread or twisted cord (15) remains placed upon the vesical neck (22) and the external handle (9) remains with its inside end upon the head of the worm (3) and whose opposite end outside the body, this arrangement permitting the adjustment of the thread or twisted cord (15) upon the vesical neck (22) to be done in a precise manner, during surgery itself as well as afterwards in the postoperative period.

When the adjustment of the thread or twisted cord (15) upon the vesical neck suffices to avoid urinary incontinence, the external handle (9) will be removed.

If once the external handle (9) has been removed and the wound has healed there is incontinence again, a small incision with local anesthesia suffices so that by means of a small screwdriver or specific tool, the thread or twisted cord (15) is adjusted again.

Likewise, once surgery has taken place and the correct adjustment of the thread or twisted cord (15) upon the vesical neck (22) has been made, the external handle (9) can be replaced by a guide thread (18) during the postoperative period and in the event that urinary incontinence occurs it will be inserted in the laparatomy incision when the external handle (16) whose end (17) will connect to the head of the worm (3) is adjusted, in order to adjust the thread or twisted cord (15) on the vesical neck (22.)

Likewise, the rigid external handle (9) can be replaced by a flexible tube (19) in whose inside end the hollow body, with body (21) inside it, in order to be coupled upon the head of the worm (3,) is coupled.

When the thread or twisted cord (15) is to be adjusted, the part of the flexible thread (19) that projects from the body will be actuated. When the handle is to be released, a screwdriver or similar element will be inserted inside the tube (19) so that the release takes place when the body (21) is actuated.

The mechanical device to correct urinary incontinence in women achieves the following advantages:

* Exact adjustment of the pressure exerted on the vesical neck in order to have a suitable urethro-vesical angle that prevents incontinence.

* Shortening the duration of surgery. It is only necessary to pass the thread or twisted cord through the mechanical system, fasten it and afterwards carry out the adjustment during surgery. If a few days later there is incontinence or on the contrary a retention of urine, it will suffice to actuate the external handle in order to correct this situation.

* The vesical catheter can be removed a few days after the operation due to the continuous control of the tightness of the thread or twisted cord.

* Upon adjusting the twisted cord or thread rubbing with tissues is avoided, given that the two ends of the know simultaneously leave and enter the tightening system.

If there is incontinence a few months later, it suffices to make a small incision with local anesthesia in order to make the adjustment again with a screwdriver.

What is claimed:

1. A device for correcting urinary incontinence in female patients comprising:

a housing having an enclosure, said housing having a first through duct and a second through duct, said first and second through ducts each establishing communication from within said enclosure to outside of said device;

a drum being rotatably mounted within said enclosure of said housing;

a toothed wheel being disposed within said enclosure and being connected to said drum;

a worm gear being disposed within said housing and having a head, said worm gear meshing with said toothed wheel;

a thread having a first end and a second end, said first end passing through said first through duct and being connected to said drum, said second end passing through said second through duct and being connected to said drum;

an external handle having a first end and a second end, said external handle first end having a means for receiving an actuating force, said external handle second end having means for coupling to said head of said worm gear to transmit said actuating force thereto.

2. A device according to claim 1, wherein the external handle is connected to and partially mounted within a flexible hollow tube, said external handle first end protruding outside of said flexible hollow tube, said external handle second end being disposed within said flexible hollow tube.

3. A device for correcting urinary incontinence in female patients comprising:

a housing having an enclosure, said housing having a first through duct and a second through duct, said first and second through ducts each establishing communication from within said enclosure to outside of said device;

a drum being rotatably mounted within said enclosure of said housing;

a toothed wheel being disposed within said enclosure and being connected to said drum;

a worm gear being disposed within said housing and having a head, said worm gear meshing with said toothed wheel;

a thread having a first end and a second end, said first end passing through said first through duct and being connected to said drum, said second end passing through said second through duct and being connected to said drum;

a guide thread being connected to said head of said worm gear, said guide thread having means for guiding a handle to said head of said worm gear.

* * * * *